US012788643B2

(12) United States Patent
O'Connell et al.

(10) Patent No.: US 12,788,643 B2
(45) Date of Patent: Nov. 10, 2026

(54) ABSORBENT SYSTEMS AND ABSORBENT ARTICLES INCLUDING THE SAME

(71) Applicant: First Quality Baby Products, LLC, Great Neck, NY (US)

(72) Inventors: Susan O'Connell, Chesterbrook, PA (US); Berna Yalcin, King of Prussia, PA (US); Brian K. Dyer, Gray, GA (US)

(73) Assignee: First Quality Baby Products, LLC, Great Neck, NY (US)

( * ) Notice: Subject to any disclaimer, the term of this patent is extended or adjusted under 35 U.S.C. 154(b) by 535 days.

(21) Appl. No.: 18/073,040

(22) Filed: Dec. 1, 2022

(65) Prior Publication Data

US 2023/0165732 A1 Jun. 1, 2023

Related U.S. Application Data

(60) Provisional application No. 63/284,888, filed on Dec. 1, 2021.

(51) Int. Cl.

| | |
|---|---|
| ***A61F 13/15*** | (2006.01) |
| ***A61F 13/49*** | (2006.01) |
| ***A61F 13/536*** | (2006.01) |
| ***A61F 13/537*** | (2006.01) |
| *A61F 13/45* | (2006.01) |

(52) U.S. Cl.

CPC ............ *A61F 13/536* (2013.01); *A61F 13/49* (2013.01); *A61F 13/53756* (2013.01); *A61F 2013/4581* (2013.01)

(58) Field of Classification Search

CPC .. A61F 13/536; A61F 13/49; A61F 13/53756; A61F 2013/4581

See application file for complete search history.

(56) References Cited

U.S. PATENT DOCUMENTS

| | | | |
|---|---|---|---|
| 6,455,753 | B1 | 9/2002 | Glaug et al. |
| 6,852,101 | B2 | 2/2005 | Damaghi et al. |
| 7,956,236 | B2 | 6/2011 | Ponomarenko et al. |
| 9,208,138 | B2 | 12/2015 | Horiuchi et al. |
| 2005/0267429 | A1 | 12/2005 | Cohen |
| 2018/0008487 | A1* | 1/2018 | Ehrnsperger .......... A61F 13/534 |
| 2019/0201251 | A1* | 7/2019 | Rosati ...................... A61F 13/45 |
| 2020/0390615 | A1* | 12/2020 | Kreuzer ............ A61F 13/49011 |

FOREIGN PATENT DOCUMENTS

| | | | |
|---|---|---|---|
| JP | 2008284190 | A | 11/2008 |
| WO | 2009067059 | A1 | 5/2009 |

* cited by examiner

*Primary Examiner* — Jacqueline F Stephens

(74) *Attorney, Agent, or Firm* — Amster, Rothstein & Ebenstein LLP

(57) ABSTRACT

Absorbent systems having absorbent cores and acquisition distribution layers, where the absorbent cores have material free zones.

12 Claims, 5 Drawing Sheets

ABSORBENT SYSTEMS AND ABSORBENT ARTICLES INCLUDING THE SAME

RELATED APPLICATIONS

This application claims priority to and the benefit of U.S. Provisional Patent Application 63/284,888, filed Dec. 1, 2021 and entitled ABSORBENT SYSTEMS AND ABSORBENT ARTICLES INCLUDING THE SAME, the contents of which are incorporated herein by reference in their entirety.

FIELD OF THE INVENTION

The present invention generally relates to absorbent systems, and in particular to absorbent systems useful in hygienic absorbent articles.

BACKGROUND

Diapers, training pants, briefs, sanitary pads and pantiliners have been made and sold for many years. In general, these products prevent accidental contact with body fluids or feces. The products typically include an absorbent core to retain fluids. The cores may be used with acquisition distribution layers ("ADL") adjacent to, above or below the absorbent core. While generally effective in absorbing liquids, these cores may be thick, stiff, or uncomfortable. There has been a continuing interest in developing improved absorbent cores. In general, there is a desire to improve absorbency, flexibility and comfort.

Absorbent cores with channels or material free zones are known and may provide benefits in terms of fluid handling and product fit. There is a continuing need to provide improved absorbent systems.

SUMMARY OF THE INVENTION

An absorbent system according to an exemplary embodiment of the present invention comprises: an absorbent core comprising at least one material free zone; an absorbent layer beneath the absorbent core; an upper core wrap above the absorbent core; a lower core wrap beneath the absorbent layer; and an acquisition distribution layer above the upper core wrap, wherein the upper core wrap is attached to the absorbent layer through at least one material free zone of the absorbent core.

An absorbent system according to an exemplary embodiment of the present invention comprises: an absorbent core comprising at least one material free zone; an absorbent layer beneath the absorbent core; an upper core wrap above the absorbent core; a lower core wrap beneath the absorbent layer; and an acquisition distribution layer above the upper core wrap, wherein the upper core wrap does not attach to the absorbent layer through the at least one material free zone of the absorbent core.

An absorbent system according to an exemplary embodiment of the present invention comprises: an absorbent core comprising at least one material free zone; an upper core wrap above the absorbent core; a lower core wrap beneath the absorbent core; a first acquisition distribution layer above the upper core wrap; and a second acquisition distribution layer above the lower core wrap, wherein the upper core wrap does not attach to the lower core wrap through the at least one material free zone of the absorbent core.

An absorbent system according to an exemplary embodiment of the present invention comprises: a first absorbent core comprising at least one material free zone; a second absorbent core comprising at least one material free zone, wherein a size of the at least one material free zone of the second absorbent core is different from a size of the at least one material free zone of the first absorbent core; an acquisition distribution layer between the first and second absorbent cores; and a core wrap surrounding the first absorbent core.

According to an exemplary embodiment, the at least one material free zone is devoid of absorbent material.

According to an exemplary embodiment, the at least one material free zone has shape selected from the group consisting of: round, oval, elliptical, square and rectangular.

According to an exemplary embodiment, the at least one material free zone extends entirely through the thickness of the absorbent core.

According to an exemplary embodiment, the at least one material free zone comprises a plurality of material free zones.

According to an exemplary embodiment, the absorbent core is a first absorbent core and the absorbent system further comprises a second absorbent core disposed adjacent to the first absorbent core.

According to an exemplary embodiment, the second absorbent core does not contain any material free zones.

According to an exemplary embodiment, the second absorbent core comprises at least one material free zone.

According to an exemplary embodiment, the at least one material free zone of the first absorbent core has at least one of a different size or shape as compared to the at least one material free zone of the second absorbent core.

According to an exemplary embodiment, the at least one material free zone has an area of 5 $cm^2$ to 20 $cm^2$.

According to an exemplary embodiment, the at least one material free zone has a length of 5 cm to 20 cm.

According to an exemplary embodiment, the at least one material free zone has a width of 0.25 cm to 1 cm.

According to an exemplary embodiment of the present invention, a system for making an absorbent core comprises: core inserts that are placed in absorbent core forming drums to form pulp and SAP free zones in an absorbent core; a lower ADL cut and place unit configured to feed, cut and place an ADL under the core; and a press with phased inserts configured to debulk the core.

DETAILED DESCRIPTION OF PREFERRED EMBODIMENTS

Figure 1:
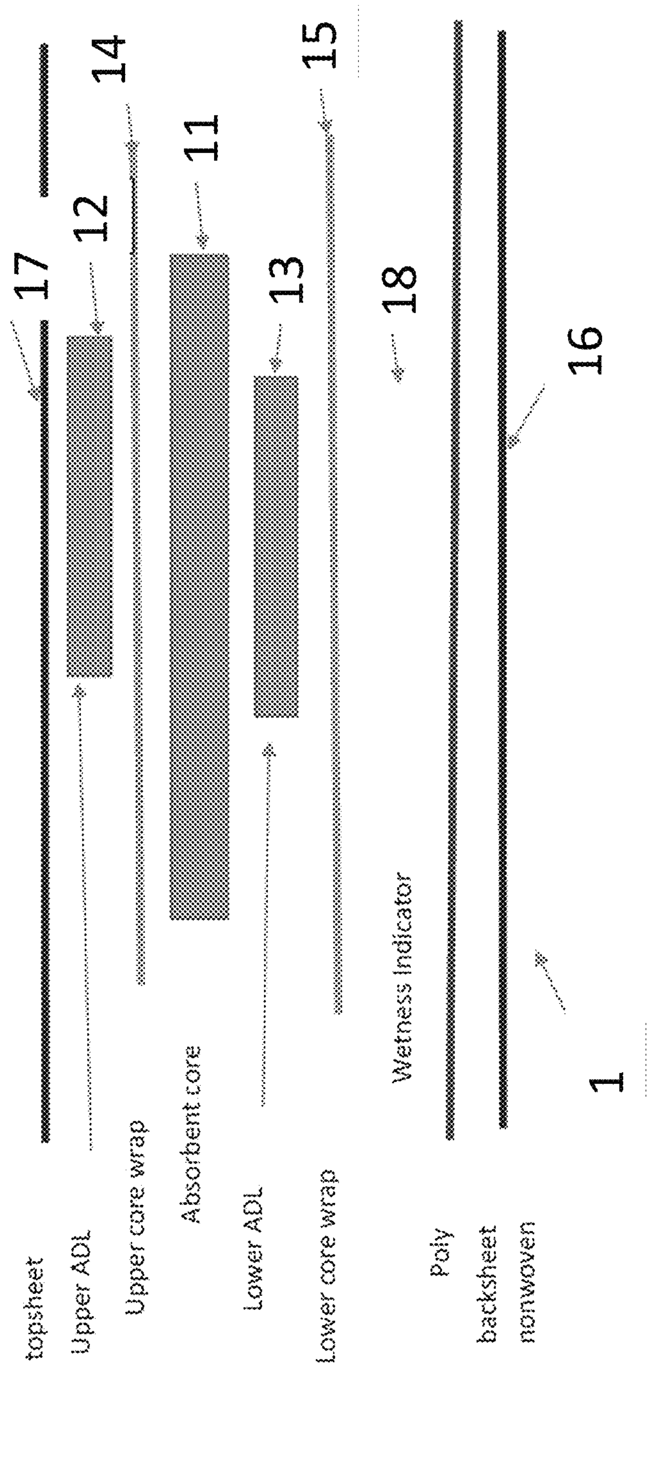
FIG. 1 is a cross-section view of an absorbent system according to an exemplary embodiment of the present invention.

Absorbent systems according to exemplary embodiments of the present invention include at least one absorbent core or insert having at least one material free zone, and upper and lower core wraps. For the purposes of the present disclosure, the term "material free zone" may be defined as a zone that is intentionally devoid of any material so as to form a void in the absorbent core or insert.

Absorbent cores or inserts may be formed or cut out from rolls of absorbent materials. As used herein, the term "absorbent core or insert" refers to a material or combination of materials suitable for absorbing, distributing, and storing aqueous fluids such as urine, blood, menses, and water found in body exudates. The size and shape of the absorbent core can be altered to meet absorbent capacity requirements, and to provide comfort to the wearer/user. The length of the absorbent core may range from about 20 cm to about 60 cm. The width of the absorbent core may range from about 4 cm to about 20 cm. When a second absorbent core is utilized, the second absorbent core may be the same size as the first core, smaller than the first core, or larger than the first core. The absorbent core suitable for use in the present invention can be any liquid absorbent material known in the art for use in absorbent articles, provided that the liquid absorbent material can be configured or constructed to meet absorbent capacity requirements. Nonlimiting examples of liquid absorbent materials suitable for use as the absorbent core include comminuted wood pulp, which is generally referred to as airfelt; creped cellulose wadding; absorbent gelling materials including superabsorbent polymers, such as hydrogel-forming polymeric gelling agents; chemically stiffened, modified, or cross-linked cellulose fibers; synthetic fibers including crimped polyester fibers; tissue including tissue wraps and tissue laminates; capillary channel fibers; absorbent foams; absorbent sponges; synthetic staple fibers; peat moss; or any equivalent material; or combinations thereof, as is well known in the art of making absorbent products such as sanitary napkins, pantiliners, incontinence pads, and the like. The amount of superabsorbent polymer in the absorbent core may range from about 20 to about 85 or about 40 to about 80 or about 50 to about 75 or about 60 to about 70 percent by weight, based on the total weight of absorbent material in the core.

In exemplary embodiments, the absorbent core may also be a coform material. The term "coform material" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles or fibers, inorganic absorbent materials, treated polymeric staple fibers and the like. Any of a variety of synthetic polymers may be utilized as the melt-spun component of the coform material. For instance, in some embodiments, thermoplastic polymers can be utilized. Some examples of suitable thermoplastics that can be utilized include polyolefins, such as polyethylene, polypropylene, polybutylene and the like; polyamides; and polyesters. In some embodiments, the absorbent system includes more than one absorbent core, for example two or three absorbent cores.

At least one absorbent core or insert includes at least one material free zone. As used herein, the term "material free zone" means that an area within the absorbent core is essentially free of absorbent material (and has limited or no absorption capacity). In exemplary embodiments, the at least one material free zone does not contain absorbent material. The material free zone may be any shape including, but not limited to, round, oval elliptical, square or rectangular and typically covers an area of from about 5 $cm^2$ to about 20 $cm^2$, and/or from about 5 cm to about 20 cm in length. The width of the material free zone may range from about 0.4 cm to about 2 cm, or from about 0.25 cm to about 1 cm. The material free zone typically extends through the thickness of the absorbent core. In some embodiments, the absorbent core has two material free zones. The absorbent core may include three, four, five, six or more material free zones. In embodiments where there is more than one absorbent core, the second and third absorbent cores may or may not include material free zones. When a second or third absorbent core includes at least one material free zone, the size and shape of the material free zone(s) may be the same as the material free zone(s) in the first absorbent core or may be different.

In exemplary embodiments, the absorbent system may include an acquisition distribution layer (ADL) for distributing liquids to the fluid-absorbent core. The ADL may be made entirely of conventional fibrous materials with little absorbency, but in some embodiments includes water-absorbent polymer particles or other absorbent materials. The fibrous material may be hydrophilic, hydrophobic or can be a combination of both hydrophilic and hydrophobic fibers. The fibrous material may be derived from natural fibers, synthetic fibers or a combination of both. Suitable ADLs are formed from cellulosic fibers and/or modified cellulosic fibers and/or synthetics or combinations thereof. Thus, suitable ADLs may contain cellulosic fibers, in particular wood pulp fluff. Modified cellulosic fibers may be utilized for fluid acquisition and distribution. Examples of modified cellulosic fibers are chemically treated cellulosic fibers, especially chemically stiffened cellulosic fibers. The basis weight of cellulosic fibers and modified cellulosic fibers may range from about 50 to about 200 gsm.

Suitable acquisition-distribution layers may further include synthetic fibers. Hydrophilic synthetic fibers may be obtained by chemical modification of hydrophobic fibers, such as by surfactant treatment of hydrophobic fibers. The surface of the hydrophobic fiber can be rendered hydrophilic by treatment with a nonionic or ionic surfactant, e.g., by spraying the fiber with a surfactant or by dipping the fiber into a surfactant.

In some embodiments, acquisition-distribution layers comprise fibrous material and water-absorbent polymer particles distributed within to function as an absorbent layer. ADLs may include from about 80% to about 100% by weight fibrous material and from 0% to about 20% or about 5% to about 15% or about 10% by weight water-absorbent polymer particles, based on the total weight of the ADL.

Alternatively, a bundle of synthetic fibers acting as an ADL loosely distributed on top of or below the fluid-absorbent core may be used. Suitable synthetic fibers include, for example, copolyester, polyamide, copolyamide, polylactic acid, polypropylene or polyethylene, viscose or blends thereof. Bicomponent fibers may also be used. In exemplary embodiments, the synthetic fiber component may be composed of either a single fiber type with a circular cross-section or a blend of two fiber types with different cross-sectional shapes.

The ADL basis weight may range from about 20 gsm to about 200 gsm, depending on the concentration of water-absorbent polymer particles. The length of upper ADLs may range from about 6 cm to about 25 cm. The width of upper ADLs may range from 4 cm to 10 cm. The length of lower ADLs may range from about 6 cm to about 60 cm. The width of lower ADLs may range from 6 cm to 15 cm.

In exemplary embodiments, a core wrap may assist with containment and integrity of the absorbent core components. The core wrap may be bonded to the absorbent core. Bonding of the core wrap to the absorbent core may occur via any means known to one of ordinary skill, such as, but not limited to, adhesives. The core wrap may be composed of separate sheets of material (such as an upper core wrap and a lower core wrap) which can be utilized to partially or fully encompass the absorbent core and which can be sealed together using a sealing means such as an ultrasonic bonder or other thermochemical bonding means, or the use of an adhesive. The core wrap may include, but is not limited to, natural and synthetic fibers such as polyester, polypropylene, acetate, nylon, polymeric materials, cellulosic materials such as wood pulp, cotton, rayon, viscose, LYOCELL® such as from Lenzing Company of Austria, or mixtures of these or other cellulosic fibers, and combinations thereof. Natural fibers may include wool, cotton, flax, hemp, and wood pulp. The material forming the core wrap may be selected from meltblown-spunbond-meltblown fabric, spunbond fabric, meltblown fabric, coform fabric, carded web, bonded-carded web, bicomponent spunbond fabric, spunlace, tissue, and combinations thereof. Further, the core wrap may be made of a spunbond-meltblown-spunbond ("SMS") material, such as a 9 gsm spunbond-meltblown-spunbond material.

The core wrap may be less hydrophilic than the absorbent core, but sufficiently porous to permit body fluids to penetrate through the core wrap to reach the absorbent core. The core wrap may have sufficient structural integrity to withstand its own wetting and the wetting of the absorbent core. In order to support this functional property of the core wrap, a wet strength agent may be applied to the core wrap. A non-limiting example of a wet strength agent may be Kymene 6500 (557LK) or equivalent available from Ashland Inc, of Ashland, Ky., Similarly, a surfactant may be included in the core wrap to promote hydrophilicity.

The upper and lower core wraps may be attached at the sides adjacent to the core (sandwich attachment) or in a C wrap configuration. With the C wrap configuration, the upper core wrap may fold around and under the bottom of the core, where it is attached to the lower core wrap. Alternatively, the lower core wrap may fold around and over the upper of the core, where it is attached to the upper core wrap. In some embodiments, the absorbent system does not include a core wrap.

The absorbent systems may be useful for, for example, diapers, training pants, youth pants, briefs, sanitary pads, bladder control pads and the like. In use, the absorbent systems of exemplary embodiments of the present invention are placed on a top surface of a backsheet. Backsheets are materials that generally are liquid impermeable but may be moisture vapor permeable (breathable). Backsheets are used in absorbent products on a surface of the product that is distal to the user's body. The backsheet can be made of any known or otherwise effective backsheet material, provided that the backsheet prevents external leakage of exudates absorbed and contained in the protective underwear. Flexible materials suitable for use as the backsheet include, but are not limited to, woven and nonwoven materials, laminated tissue, polymeric films such as thermoplastic films of polyethylene and/or polypropylene, microporous films, composite materials such as a film-coated nonwoven material, or combinations thereof, as is well known in the art of making absorbent products, such as sanitary napkins, pantiliners, incontinence pads, and the like.

The absorbent system is typically attached to the backsheet with an adhesive. Suitable adhesives are known in the art and include hot melt adhesives, emulsion polymer adhesives and the like.

A topsheet or cover is placed on top of the absorbent system and attached to the core or insert and backsheet with adhesive, ultrasonic bonding or combinations thereof, forming a chassis. Suitable topsheets are compliant, soft feeling, and non-irritating to the body of the wearer. Suitable topsheet materials include a liquid pervious material that is oriented towards and contacts the body of the wearer, thereby permitting body discharges to rapidly penetrate through the topsheet without allowing fluid to flow back through the topsheet to the skin of the wearer. A suitable topsheet can be made of various materials, such as woven and nonwoven materials; apertured film materials including apertured formed thermoplastic films, apertured plastic films, and fiber-entangled apertured films; hydro-formed thermoplastic films; porous foams; reticulated foams; reticulated thermoplastic films; thermoplastic scrims; or combinations thereof, as is well known in the art of making absorbent products such as sanitary napkins, pantiliners, incontinence pads, protective underwear and the like.

Elastic side panels may be attached to the chassis to form diapers or adult protective underwear. Any elastic side panel known in the art of absorbent articles may be useful. Suitable elastic side panels include laminates of elastic films with nonwovens, laminates of elastic strands with nonwovens and the like. The elastic panels may be attached to the chassis by adhesive, ultrasonic bonding or a combination thereof. The length, width and shape of the side panels may be designed to make products of different sizes. Products with side panels may have a more underwear like appearance.

The side panels are then attached to the insert/core. A portion of each side panel is left unattached to form leg openings. The side panels may be attached to the insert/core with glue, adhesive, ultrasonic bonding or combinations thereof. The side panels may be attached to the insert/core at various angles to create a more garment like fit.

As is known in the art, hooks and loops may be used on articles in accordance with exemplary embodiments of the present invention. Nonwoven materials may function as the loops.

In exemplary embodiments, the hook fasteners may be made up of separate hook elements or may be integral with the side panels. In this regard, the hook elements may be bonded to the side panels by adhesive, ultrasonic, thermal bonding or the like. Alternatively, the hook elements may be intimately joined with the material that forms the side panels. Such intimate bonding of hook elements with a layer of material may be accomplished by feeding extruded plastic and a sheet of material through a nip formed by a first roller having pins and a second roller having corresponding cavities. As the molten plastic is forced through the nip, it flows into the cavities of the second roller and also into pores in the sheet of material. The plastic in the cavities cools and hardens so as to form a hook sheet. At the same time, the sheet of material is intimately joined to and becomes an integral part of the hook sheet so as to form a laminated structure. This process is disclosed in U.S. Pat. No. 5,518,795, the contents of which are incorporated herein by reference in their entirety. The hook elements may be arranged on the side panels in longitudinally extending strips that are laterally spaced from one another. Alternatively, the hook elements may be arranged in a pattern of geometric shapes or lines. Desirably, the hook elements are arranged on an inelastic material in order to improve ease of processing and the shear strength of the seam.

Figure 3:
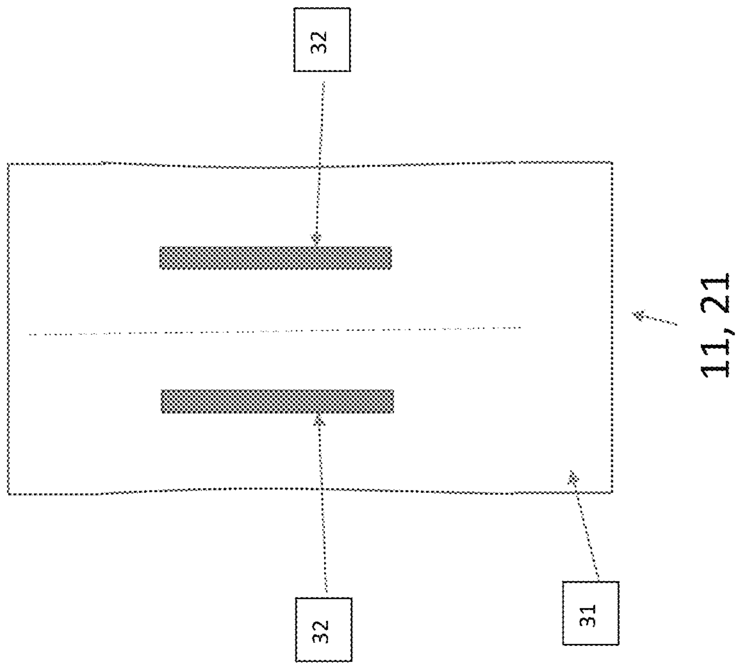
FIG. 3 is a top view of an absorbent system according to an exemplary embodiment of the present invention.

FIG. 1 shows an absorbent system, generally designated by reference number 1, according to an exemplary embodiment of the present invention. As shown in FIG. 1, the absorbent system 1 includes an absorbent core 11. The absorbent core 11 includes two rectangular material free zones 32 as shown in FIG. 3. The length of each material free zone 32 is 10.5 cm and the width of each material free zone is 0.8 cm. An upper ADL 12, which in this embodiment is not absorbent and a lower ADL 13, which in this embodiment is absorbent are positioned above an upper core wrap 14 and a lower core wrap 15, respectively. A backsheet 16 is provided below the absorbent core 11, the upper and lower ADLs 12, 13, and the upper and lower core wraps 14, 15. The backsheet 16 may be printed with a color change wetness indicator 18. The lower core wrap 15, lower ADL 13, absorbent core 11, upper core wrap 14 and upper ADL 12 are placed on the backsheet. The upper core wrap 14 is attached to the lower core wrap 15 on sides adjacent to the core (sandwich wrap) by adhesives, thermal bonding, ultrasonic bonding or combinations thereof. The upper core wrap 14 may be attached to the lower absorbent ADL 13 by adhesive, thermal bonding, ultrasonic bonding or combinations thereof. A cover or topsheet 17 is disposed over the other components of the absorbent system 1 and sealed to the backsheet 16.

Figure 2:
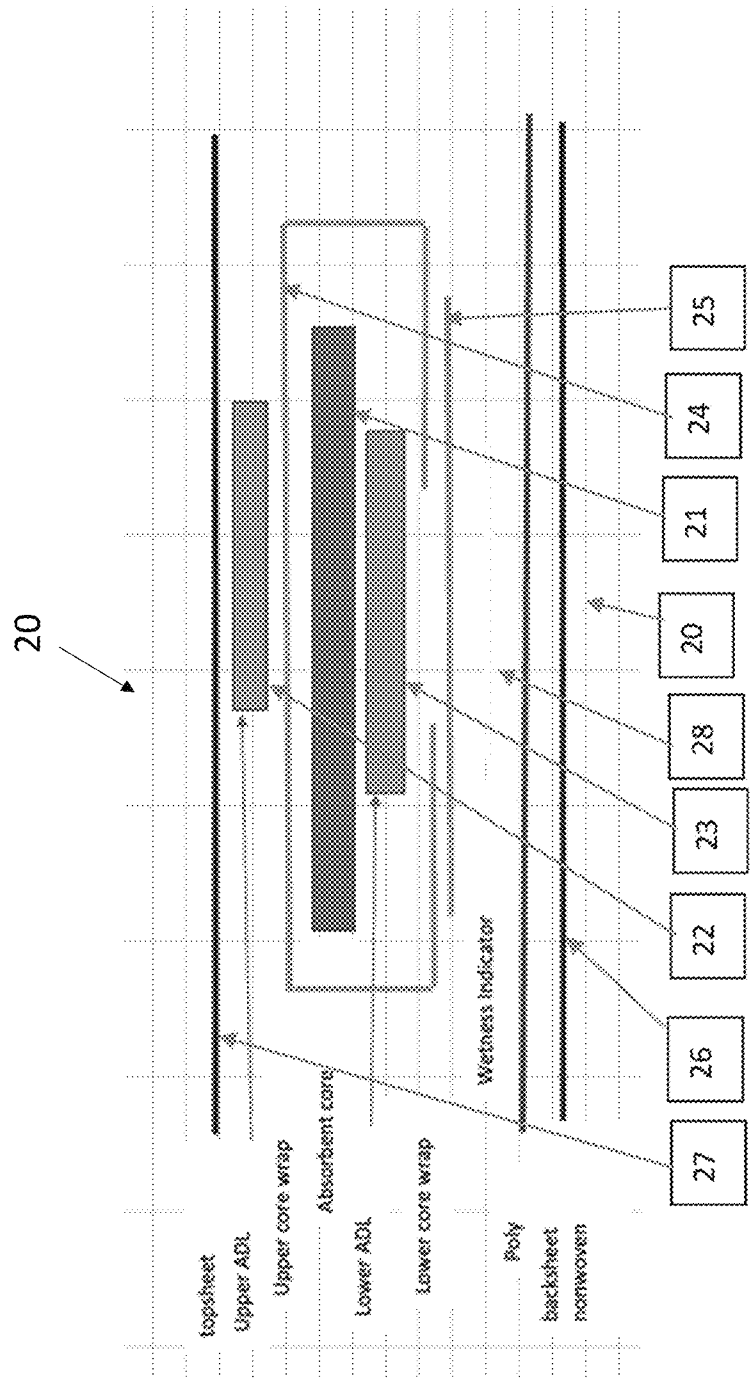
FIG. 2 is a cross-section view of an absorbent system according to another exemplary embodiment of the present invention.

FIG. 2 shows an absorbent system, generally designated by reference number 20, according to an exemplary embodiment of the present invention. As shown in FIG. 2, the absorbent system 20 includes an absorbent core 21. The absorbent core 21 includes two rectangular material free zones as shown in FIG. 3. The length of each material free zone is 10.5 cm and the width of each material free zone is 0.8 cm. An upper ADL 22, which in this embodiment is not absorbent and a lower ADL 23, which in this embodiment is not absorbent are positioned above an upper core wrap 24 and a lower core wrap 25, respectively. A backsheet 26 is provided below the absorbent core 21, the upper and lower ADLs 22, 23, and the upper and lower core wraps 24, 25. The backsheet 26 may be printed with a color change wetness indicator 28. The lower core wrap 25, lower ADL 23, absorbent core 21, upper core wrap 24 and upper ADL 22 are placed on the backsheet 26. The upper core wrap 24 is not directly attached to and does not directly contact the lower ADL 23. The upper core wrap 24 is attached to the lower core wrap 25 underneath the core (C wrap) with adhesive, thermal bonding, ultrasonic bonding or combinations thereof. A cover or topsheet 27 is disposed over the other components of the absorbent system 20 and sealed to the backsheet 26.

FIG. 3 shows absorbent core 11, 21 having absorbent material 31 and material free zones 32, which in this case are rectangular shaped with a length of 11.5 cm and a width of 0.4 cm.

Figure 4:
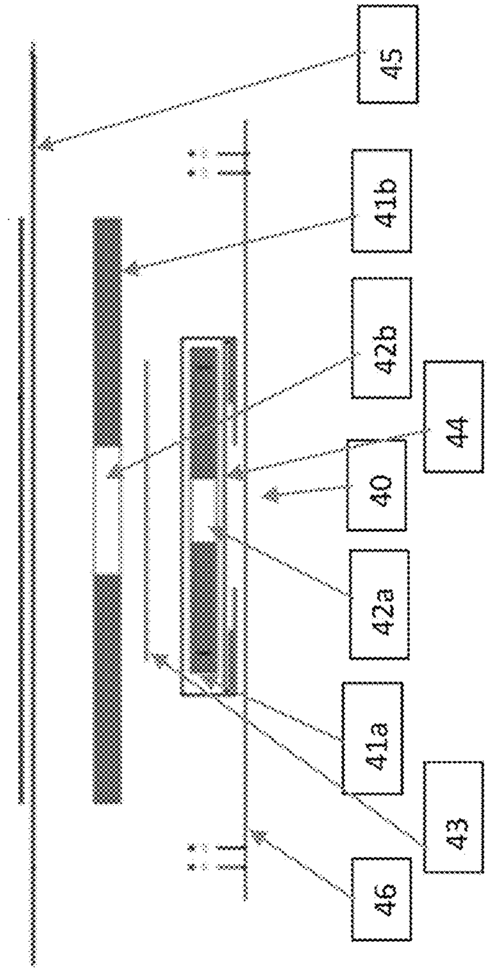
FIG. 4 is a cross-section view of an absorbent system according to another exemplary embodiment of the present invention, where the absorbent system is useful for bladder control pads.

FIG. 4 shows a bladder control pad absorbent system, generally designated by reference number 40, according to an exemplary embodiment of the present invention. The absorbent system 40 includes a first absorbent core 41*a* disposed below and a second absorbent core 41*b*. Each of the first and second absorbent cores 41*a* and 41*b* include material free zones 42*a* and 42*b*. The upper core is 35.5 cm long and 10 cm wide. The lower core is 45.5 cm long and 10 cm wide. The material free zone 42*b* in the second core 41*b* is 12.5 cm long and 0.8 cm wide. The material free zone 42*a* in the first core 41*a* is 12.5 cm long and 0.8 cm wide. The first absorbent core 41*a* is surrounded by core wrap 44. The first absorbent core 41*a* may be directly attached to a backsheet 46. An ADL 43 is positioned between the first and second cores 41*a*, 41*b*. A topsheet or cover 45 is disposed over the other components of the absorbent system 40 and attached to the backsheet 46.

In exemplary embodiments, absorbent systems of the present invention provide absorbent products with absorbency, fit and comfort.

Conventional absorbent core machines for making diapers and protective underwear may be modified with a kit to make products according to exemplary embodiments of the present invention. The kit may include core inserts that are placed in pockets of forming drums to form pulp and SAP free zones in a core; a lower ADL cut and place unit for feeding, cutting and placing an ADL under the core; and a press with phased inserts for debulking the core. The kit may also include a core wrapping section. A press section for pressing the upper core wrap down through the pulp free areas using phased inserts to attach the upper core wrap to the ADL or lower core wrap may also be included in the kit.

Figure 5:
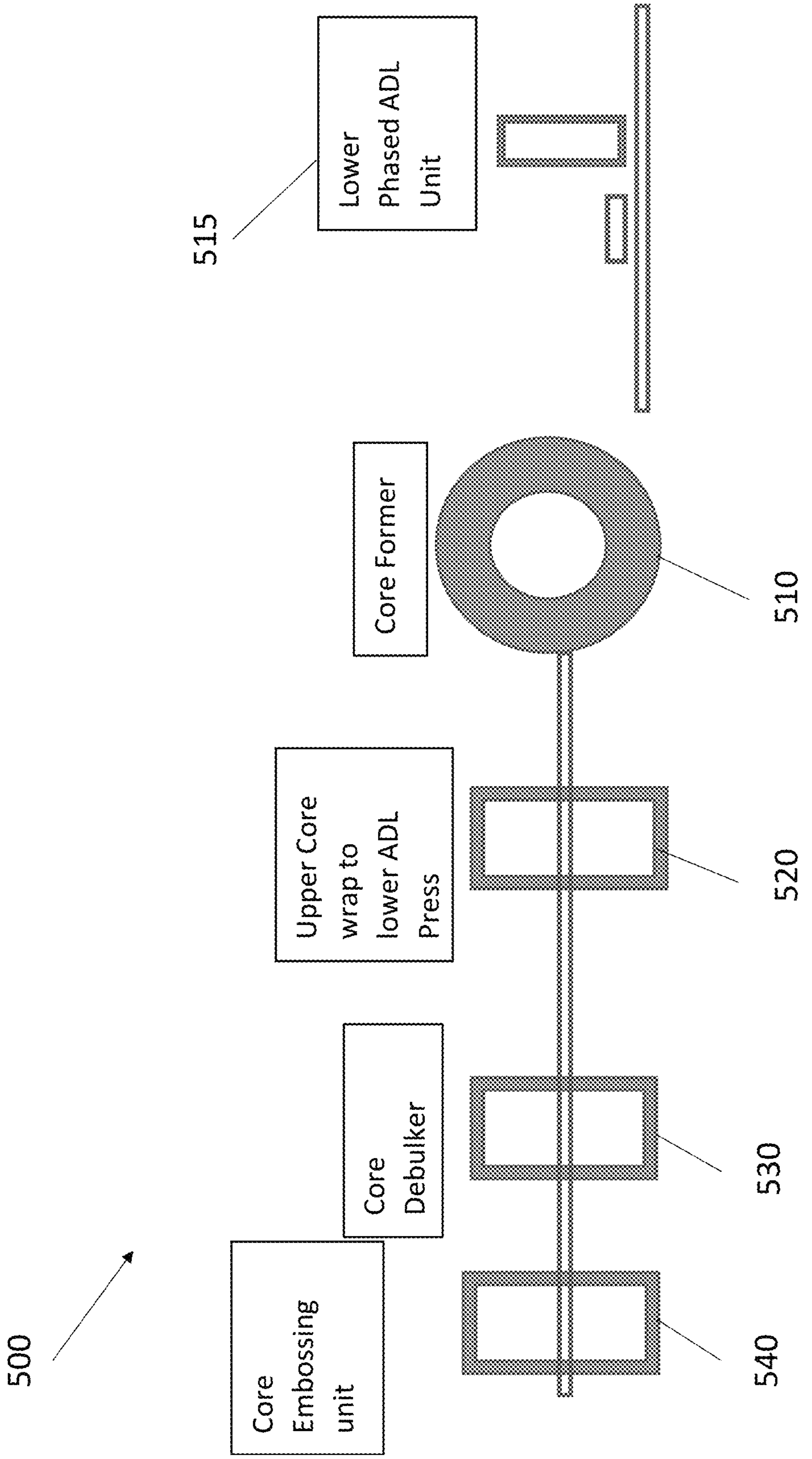
FIG. 5 is a block diagram of a system for making an absorbent system according to an exemplary embodiment of the present invention.

FIG. 5 shows a system, generally designated by reference number 500, for making a diaper core in accordance with an exemplary embodiment of the present invention. A diaper core may be formed on a forming drum 510. As known in the art, forming drums 510 include pockets that form the structural shape of the individual absorbent cores of a core web. In an exemplary embodiment, inserts may be placed into the pockets on the forming drum 510 to create pulp and SAP-free zones in the cores. For example, inserts may be used to form absorbent cores with two pulp and SAP-free zones. The diaper core is formed on an upper non-woven core wrap, or formed in the pocket and transferred to the upper non-woven core wrap. As the core web leaves the forming drum, a lower core wrap with a glued ADL phased to align with the pulp and sap free zones is applied to the core web using a lower phased ADL unit 515 to create a fully wrapped core with ADL under the pulp and sap core. The core web then travels through a first press section 520 that presses the upper core wrap down through the pulp free areas using phased inserts to attach the upper wrap to the lower wrap, then the core travels to a debulker section 530 with additional phased inserts to debulk the core. The debulker section 530 may include a second press section. The core web then travels to a third press section 540 that embosses a pattern over the wrap areas as a final process step.

Now that embodiments of the present invention have been shown and described in detail, various modifications and improvements thereon can become readily apparent to those skilled in the art. Accordingly, the exemplary embodiments of the present invention, as set forth above, are intended to be illustrative, not limiting. The spirit and scope of the present invention is to be construed broadly.

We claim:

1. An absorbent system comprising:

an absorbent core comprising at least one material free zone;

an upper core wrap above the absorbent core;

a lower core wrap beneath the absorbent core;

a first acquisition distribution layer above the upper core wrap; and a second acquisition distribution layer above the lower core wrap, wherein the upper core wrap does not attach to the lower core wrap through the at least one material free zone of the absorbent core.

2. The absorbent system of claim 1, wherein the at least one material free zone is devoid of absorbent material.

3. The absorbent system of claim 1, wherein the at least one material free zone has shape selected from the group consisting of: round, oval, elliptical, square and rectangular.

4. The absorbent system of claim 1, wherein the at least one material free zone extends entirely through the thickness of the absorbent core.

5. The absorbent system of claim 1, wherein the at least one material free zone comprises a plurality of material free zones.

6. The absorbent system of claim 1, wherein the absorbent core is a first absorbent core and the absorbent system further comprises a second absorbent core disposed adjacent to the first absorbent core.

7. The absorbent system of claim 6, wherein the second absorbent core does not contain any material free zones.

8. The absorbent system of claim 6, wherein the second absorbent core comprises at least one material free zone.

9. The absorbent system of claim 8, wherein the at least one material free zone of the first absorbent core has at least one of a different size or shape as compared to the at least one material free zone of the second absorbent core.

10. The absorbent system of claim 1, wherein the at least one material free zone has an area of 5 $cm^2$ to 20 $cm^2$.

11. The absorbent system of claim 1, wherein the at least one material free zone has a length of 5 cm to 20 cm.

12. The absorbent system of claim 1, wherein the at least one material free zone has a width of 0.25 cm to 1 cm.

* * * * *